United States Patent [19]

Shaibani et al.

[11] Patent Number: 5,571,107

[45] Date of Patent: Nov. 5, 1996

[54] LASER SURGICAL APPARATUS FOR SCULPTING A CORNEA USING A DIFFRACTIVE OPTICAL ELEMENT AND METHOD OF USING THE SAME

[76] Inventors: Sanan B. Shaibani, 1629 Washington Ave., Apt. #8, New Orleans, La. 70130; Bahram Khoobehi, 2020 Gravier, Ste. B, New Orleans, La. 70112-2234; John S. Morvant, Jr., 4 F Rue Chardonnay, Kenner, La. 70065

[21] Appl. No.: 303,219

[22] Filed: Sep. 8, 1994

Related U.S. Application Data

[63] Continuation-in-part of Ser. No. 143,087, Oct. 26, 1993, Pat. No. 5,376,086.

[51] Int. Cl.$^6$ ........................................ A61B 17/36
[52] U.S. Cl. ........................ 606/4; 606/10; 606/11
[58] Field of Search .......................... 606/3, 4, 5, 6, 606/10, 11, 12

[56] References Cited

U.S. PATENT DOCUMENTS

| | | | |
|---|---|---|---|
| 4,732,148 | 3/1988 | L'Esperance, Jr. | 128/303.1 |
| 4,856,513 | 8/1989 | Muller | 128/303.1 |
| 4,911,711 | 3/1990 | Telfair et al. | 606/5 |
| 4,994,058 | 2/1991 | Raven et al. | 606/5 |
| 5,219,344 | 6/1993 | Yoder, Jr. | 606/5 |
| 5,277,911 | 1/1994 | Viegas et al. | 606/5 |
| 5,350,374 | 9/1994 | Smith | 606/5 |
| 5,376,086 | 12/1994 | Khoobehi et al. | 606/4 |
| 5,395,356 | 3/1995 | King et al. | 606/4 |

FOREIGN PATENT DOCUMENTS 8831135801 11/1988 European Pat. Off. .......... A61F 9/00

OTHER PUBLICATIONS

Steven E. Wilson, M. D. and Stephen D. Klyce, PH.D., Advances in the Analysis of Corneal Topography, Jan., Feb., 1991, Survey Opthamology vol. 35, No. 4.

Seiji Fukushima, Takashi Kurokawa and Masayoshi Ohno, Ferroelectric Liquid–Crystal Spatial Light Modulator Achieving Bipolar Image Operation and Cascadability, Nov., 1992, Applied Optics, vol. 31, No. 32.

Jack M. Younse, Mirrors on a Chip, Nov., 1993, IEEE Spectrum.

Nobukazu Yoshikawa and Toyohiko Yatagai, Phase Optimization of a Kinoform by Simulated Annealign, Feb. 10, 1994, Applied Optics, vol. 33, No. 5.

*Primary Examiner*—Angela D. Sykes
*Assistant Examiner*—Sonya Harris-Ogugua
*Attorney, Agent, or Firm*—Haverstock, Garrrett and Roberts

[57] ABSTRACT

An apparatus for profiling a cornea of an eye is disclosed which comprises a topography instrument for determining the curvature of the cornea, a computer system for receiving information from the topography instrument for determining whether any areas of the cornea need to be ablated to correct for any abnormalities of the cornea, a diffractive optical element which is constructed based upon the determination of which areas of the cornea need to be ablated, and a beam of radiation being projected at the diffractive optical element for the diffractive optical element to modulate the beam of radiation and direct the modulated beam of radiation at the cornea for ablating the cornea to correct for any abnormalities of the cornea.

12 Claims, 5 Drawing Sheets

ABSTRACT# LASER SURGICAL APPARATUS FOR SCULPTING A CORNEA USING A DIFFRACTIVE OPTICAL ELEMENT AND METHOD OF USING THE SAME

CROSS REFERENCE TO RELATED APPLICATION

This application is a continuation-in-part of application Ser. No. 08/143,087 filed on Oct. 26, 1993, now U.S. Pat. No. 5,376,086.

BACKGROUND OF THE INVENTION

The present invention relates to an ophthalmological surgery apparatus and methods and more particularly to a laser surgical apparatus for sculpting a cornea using a diffractive optical element (DOE) and methods of using the laser surgical apparatus.

The human eye includes two focusing elements which are the cornea and the lens. The corneal tear/air interface is the major refracting surface in the eye with an average thickness refractive power of 48.8 diopters (D). The refractive power of the cornea primarily depends on the curvature of the anterior surface. In order to correct abnormal refractive conditions of the eye surgical alteration or sculpting of the shape or curvature of the cornea has been employed. Corneal sculpting involves the removal of external layers of the cornea that affects the radius of curvature of the cornea. Altering the radius of curvature of the cornea increases or decreases the dioptric power of the front surface of the cornea that corrects any abnormal refractive errors. In recent years considerable advancement in low wavelength lasers has opened frontiers in refractive surgery allowing for reshaping of the surface of the cornea by employing such lasers.

Many methods have been suggested for reprofiling of the cornea. One such suggested technique employs the use of a low wavelength excimer laser to perform controlled ablative photodecomposition. Although altering the curvature of the outer corneal surface has been effective in correcting spherical myopia, the limitation with current laser technology is the inadequacy of corrective surgery in aspheric, irregularly astigmatic corneal surfaces.

Some disclosures that relate generally to the sculpting of a patient's cornea include U.S. Pat. No. 4,911,711 entitled "Sculpting Apparatus for Correcting Curvature of the Cornea" which discusses using an ultraviolet laser for sculpting the cornea to achieve optical correction through a newly shaped anterior surface of the cornea. The apparatus subjects the laser beam to certain shaping and homogenizing operations prior to any attempt to specially characterize the beam for a particular sculpting procedure. In a preferred embodiment, the shaping and homogenizing operations present a tolerably homogeneous beam of enlarged dimension, so that specialty characterizing may proceed on a dimensional scale that is greater than the corresponding dimension of ultimate surgical delivery to the eye, thereby enabling greater control of the quality of specialty characterizing. Provision is made for selectively monitoring the quality of the homogeneity and/or the specially characterized beam, with further provision for automatic cutoff of a laser beam delivery to any eye in the event that quality is not within the predetermined limits of tolerance. Preferably, all beam shaping, homogenizing, and characterizing operations proceed in a controlled environment.

U.S. Pat. No. 4,994,058 entitled "Surface Shaping Using Lasers" issued to Anthony Raven et al discloses a laser system and masking apparatus for reprofiling surfaces, such as corneal surfaces. The system includes a laser and a mask disposed between the laser and the surface to be reprofiled, the mask providing a predefined profile of resistance to laser radiation, such that upon irradiation, part of the radiation is selectively absorbed and part is transmitted to the surface of the eye in accordance with the masked profile to selectively erode the surface. The masking apparatus disclosed is a mask that may be affixed to the surface of the eye or may include a support structure to support and position the mask above the surface. The resistance profile is stated as created by varying the thickness or the composition of the mask.

U.S. Pat. No. 4,732,148 discloses the use of ultraviolet laser radiation to control ablation of the cornea. The control of laser flux results from controlled change of projected laser-spot size in the course of a given treatment. The spot size ranges from a maximum which covers the entire area to be treated to a tolerable minimum diameter.

Although many methods have been used or are under investigation for reprofiling the surface of the cornea using laser radiation, these methods do not allow controlled variation in the output flux. Therefore, it would be advantageous to provide an apparatus that allows for manipulation and modification of the irradiated flux density profile over the entire area to be treated. Through the use of corneal topography information and diffraction theory a diffractive optical element (DOE) can be designed to control the output flux density profile of a sculpting beam. By employing a DOE to control the output flux density profile of a sculpting beam predictable and controllable corneal sculpting can be accomplished.

SUMMARY OF THE INVENTION

The present invention improves upon existing laser ablation technology by allowing the system operator to alter surfaces such as a patient's cornea to correct ametropic conditions such as myopia, hyperopia, and regular astigmatism in the presence of irregular astigmatism. The present invention achieves these objectives by modulating the flux density distribution of a laser beam by introducing into the path of the laser beam a diffractive optical element (DOE) which has a matrix of elements for regulating the incident wavefront. The matrix of elements has a predetermined distribution and arrangement. By controlling the incident wavefront, the present invention will enable the operator to reshape the topography of the surface of the cornea.

The present invention uses surface profile information generated by computer assisted topography to create an ablation profile which will yield the desired topographic changes to correct for refractive abnormalities of the eye. Based on the ablation profile, the DOE will generate a flux density distribution over the surface of the cornea by modulating the incident wavefront.

The DOE consists of a matrix of elements with at least one of the individual elements being either reflective or transmissive. Each of the elements can also have the capability of shifting the phase or amplitude of the incident wavefront. Each element within the DOE matrix will modulate the incident wavefront of a predetermined phase and amplitude at the surface to be ablated. The resultant modulated sum of the wavefronts produced by the matrix of elements will generate the flux distribution profile approximately equal to the desired ablation profile flux density distribution to allow controlled sculpting of the corneal surface. The modulation of the flux density of the incident beam will be accomplished by using optical principles of diffraction, reflection, and absorption. The device of the present invention may be configured to operate in the near-field or the far-field.

If the desired resolution cannot be achieved at the corneal surface by the use of a single DOE, a complementary DOE can be used either in series or in parallel. In the case of the series use of the DOE, multiple diffractive optical elements can be used sequentially. Alternatively, a multiple diffractive optical element can be placed in parallel to provide greater control over the flux density distribution. Other elements such as vibrating platforms or focusing elements can be used to improve the final ablation flux density at the corneal surface.

In one form, the present invention is an apparatus for profiling a cornea of an eye which comprises means for producing a diffractive optical element which is representative of the profile of the cornea to be ablated and means for projecting a beam of radiation at the diffractive optical element and the diffractive optical element producing a modulated beam which is directed at the cornea for selectively ablating the cornea for profiling the cornea to correct for any abnormalities of the cornea.

In another form, the present invention is an apparatus for profiling a cornea of an eye which comprises a topography instrument for measuring the curvature of the cornea, a computer system connected to the topography instrument for receiving information from the topography instrument which is representative of the curvature of the cornea and for determining whether any areas of the cornea need to be ablated to correct for any abnormalities of the cornea, a diffractive optical element which is representative of the profile of the cornea to be ablated, and a beam of radiation projected at the diffractive optical element for the diffractive optical element modulating the beam of radiation and projecting the modulated beam of radiation at the cornea to ablate the cornea for profiling the cornea to correct for any abnormalities of the cornea.

In light of the foregoing comments, it will be recognized that a principal object of the present invention is to provide an improved system for reprofiling the cornea of the eye.

A further object of the invention is to provide an ophthalmological surgery apparatus for surgically modifying optical properties of the eye through selected ablation of the outer surface of the cornea.

Another objection of the invention is to provide an ophthalmological surgery apparatus for safely applying laser radiation when surgically operating upon the outer surface of the cornea.

These and other objects and advantages of the present invention will become apparent after considering the following detailed specification in conjunction with the accompanying drawings, wherein:

DETAILED DESCRIPTION OF THE PREFERRED EMBODIMENTS

Figure 1:
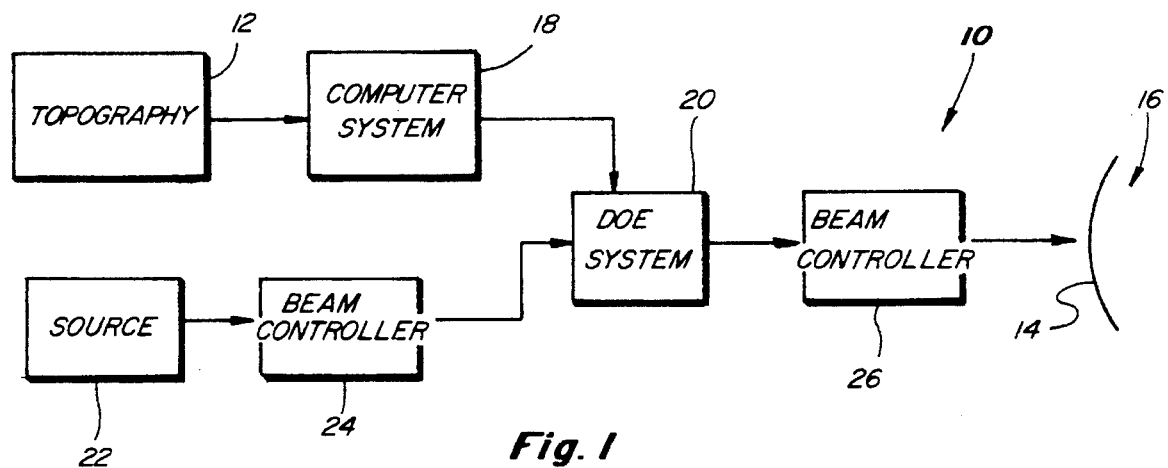
FIG. 1 is a diagrammatic illustration of an apparatus for reprofiling the surface of an eye in accordance with the present invention.

Referring now to the drawings, wherein like numerals refer to like items, number 10 identifies a preferred embodiment of an apparatus for reprofiling the surface of an eye which is constructed according to the present invention. With reference to FIG. 1, the apparatus 10 includes a topography instrument 12 which is used to analyze the topography of a cornea 14 of an eye 16. The topography instrument 12 is connected to a computer system 18 which is used to receive and analyze information, such as a dataset of values, from the topography instrument 12. The dataset of values corresponds to the profile or topography of the cornea 14. The computer system 18 is programmed to analyze the dataset of information to determine which areas on the surface of the cornea 14 need to be ablated. Once this determination has been completed, the computer system 18 provides an output to a diffractive optical element (DOE) system 20. This output includes a data matrix which is representative of the profile of the cornea to be ablated to correct the abnormal refractive errors in the eye 16.

The apparatus 10 further includes a source 22, such as a laser, which provides an output, such as a beam of light, to a beam controller 24, such as a lens or any other beam homogenizer. The source 22 may have a wavelength of 400 nanometers or less. The beam controller 24 provides an output or a beam to the DOE system 20. The DOE system 20 provides a beam to another beam controller 26. The beam provided to beam controller 26 has a flux density distribution which, when processed by the beam controller 26, will ablate the surface of the cornea 14 in a controllable manner. The flux density distribution established is that which was calculated after analysis of the eye 16 using the topography instrument 12.

Figure 2:
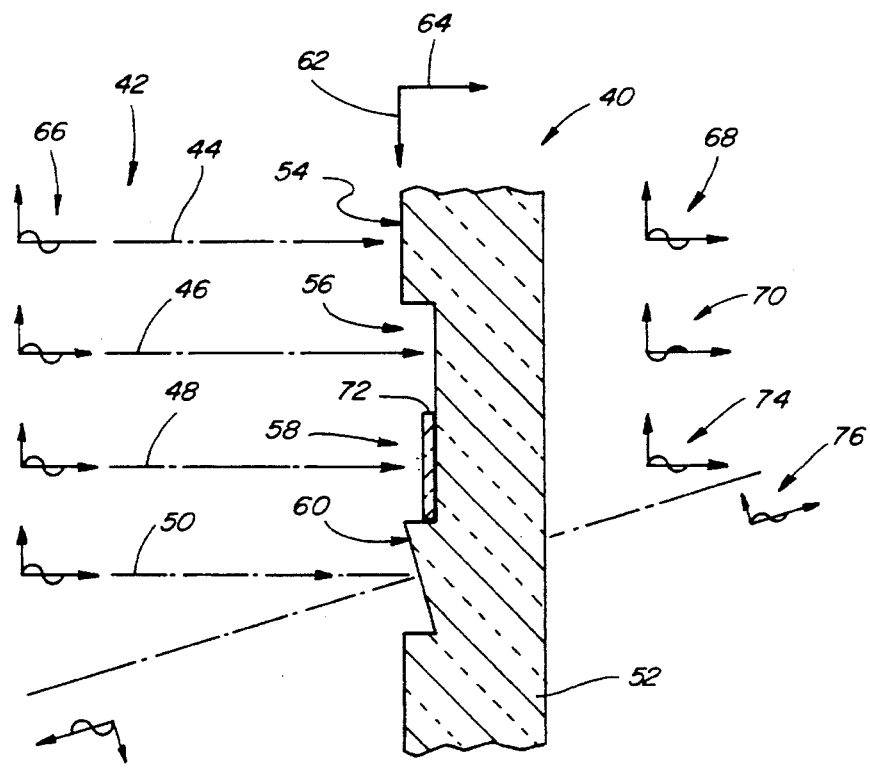
FIG. 2 is a cross-sectional view of a diffractive optical element constructed according to the present invention.

Referring now to FIG. 2, a partial cross-sectional view of a diffractive optical element (DOE) 40 which forms part of the DOE system 20 is shown. The DOE 40 is placed between the beam controllers 24 and 26 in such a manner that the beam from the beam controller 24 which is illustrated as a wavefront 42 in FIG. 2 is directed at the DOE 40. The wavefront 42 consists of light rays 44, 46, 48, and 50 which are directed at the DOE 40. The DOE 40 comprises a substrate 52 having a matrix of elements 54, 56, 58, and 60 formed thereon. The substrate 52 is constructed of a material which transmits light or which allows light to pass through. Each of the matrix of elements 54–60 has a preselected reflective index, length, width, thickness, and angle relative to a reference axis 62. In this particular figure, the reference axis 62 is shown in the −y direction and another reference axis 64 is shown in the +x direction. Reference axis 62 and reference axis 64 are orthogonal to each other as in a Cartesian coordinate system. Additionally, the DOE 40 illustrated in FIG. 2 is a transmissive type diffractive optical element in which light rays will pass through the diffractive optical element. As will be shown and discussed, it is also possible to have a reflective type diffractive optical element in which light rays are reflective by the diffractive optical element.

The light rays 44–50 of the wavefront 42 are directed at the matrix of elements 54–60. Since this DOE 40 is a transmissive type diffractive optical element, the matrix elements 54–60 modulate the incoming light rays 44–50 as the light rays 44–50 pass through the DOE 40. All of the light rays 44–50 may be represented as a signal 66 having a phase and an amplitude. As the light rays 44–50 pass through the DOE 40 the phase and amplitude of the signal 66 may be modulated. In particular, when the light ray 44 strikes matrix element 54 the phase and amplitude of a light ray emanating from the DOE 40 is essentially unchanged, as represented by a signal 68. The signal 68 is unchanged from that of signal 66 due to the thickness of the substrate 52 being an integral multiple of $2\pi$ times the wavelength of the wavefront 42. The substrate 52 at matrix element 54 is essentially transparent to the light ray 44. Element 54 is one example of one element which may be formed in the matrix of elements 54–60. Matrix element 56 is an example of another element which may be formed in the DOE 40 in which matrix element 56 shifts the phase of the signal 66 of the incoming light ray 46. The matrix element 56 has less thickness than that of matrix element 54. The output signal, as represented by a signal 70, shows that the phase of the incoming signal 66 has been shifted after it is transmitted through the DOE 40. Additionally, the amplitude of the signal 70 is the same as the amplitude of the signal 66. Matrix element 58 is an example of an element which produces an amplitude shift by changing the transparency of the substrate 52 by applying a coating 72 on the substrate 52 of the DOE 40. An output signal 74 represents an amplitude and phase shift of the incoming signal 66 of the light ray 48. Matrix element 60 is also used to change the phase and amplitude of the incoming signal 66 of light ray 50 by varying the angle of incidence of the substrate 52 with respect to the reference axis 62. The output signal, as represented by a signal 76, illustrates that both the phase and amplitude of the incoming light ray 50 are shifted. Elements 54–60 are examples of how a diffractive optical element may be constructed or fabricated to modulate an incoming light beam to be used to ablate the surface of a cornea to correct refractive errors in the cornea. The DOE 40 is constructed after taking into consideration the profile of the cornea and determining what needs to be ablated from the cornea to correct for any refractive errors in the cornea.

Figure 3:
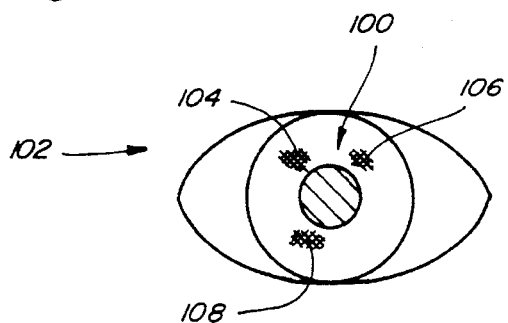
FIG. 3 is a top perspective view of an eye illustrating an ablation intensity profile.

FIG. 3 shows a typical ablation intensity profile of a cornea 100 of an eye 102 generated by using computer assisted topography. Areas 104, 106, and 108 indicate areas of the eye 102 where a higher ablation rate is required to remove portions of the cornea 100 in order to correct abnormal refractive conditions. The ablation intensity profile is determined after analysis of the profile of the cornea 100 by using computer assisted topography. Computer assisted topography is described in an article entitled "Advances in the Analysis of Corneal Topography", Survey of Ophthalmology, Volume 35, Number 4, January–February 1991, which is incorporated herein by this reference. This article also discusses some topography instruments which may be examples of the topography instrument 12 discussed with reference to FIG. 1.

Figure 4:
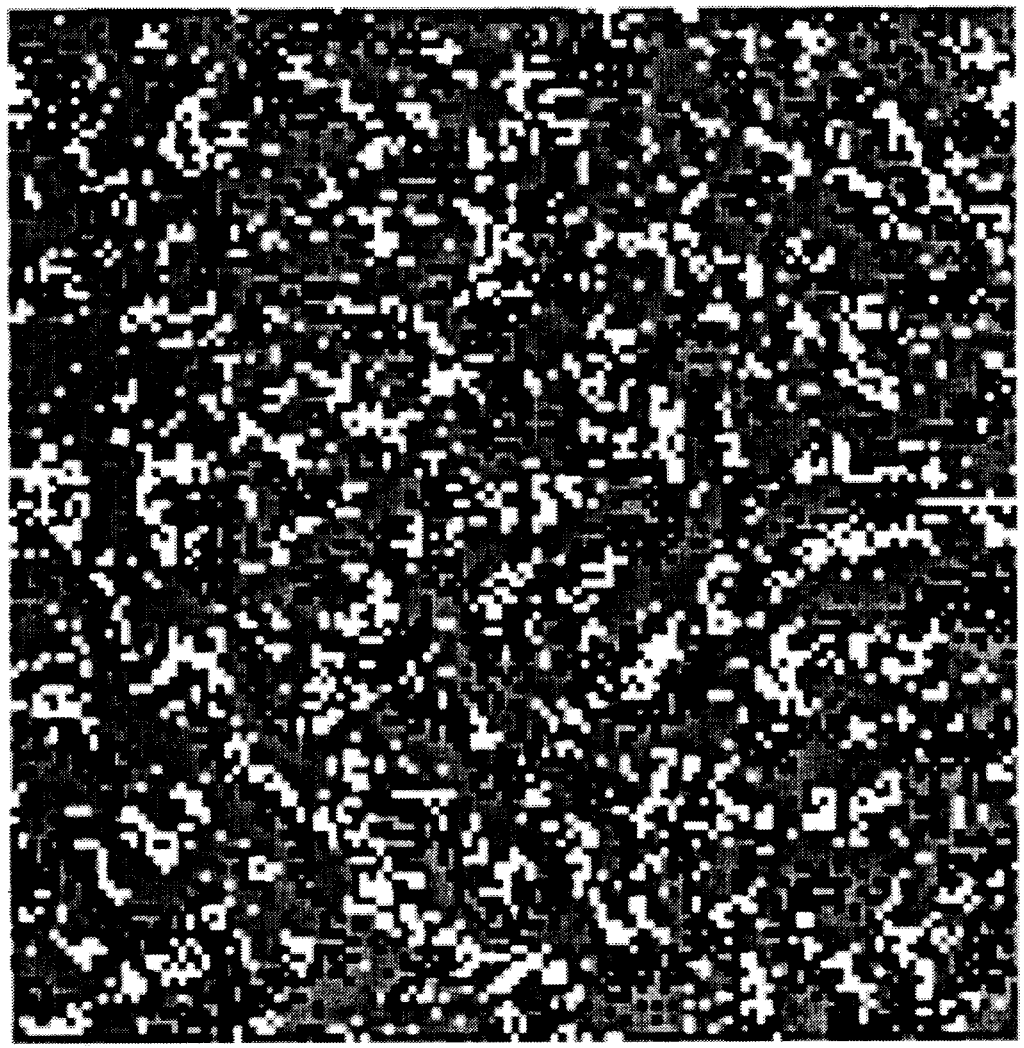
FIG. 4 is a pattern generated by the apparatus for reprofiling the surface of the eye according to the present invention.

FIG. 4 illustrates an example of a complete DOE 40 which has been constructed after analysis of a cornea to determine which areas of the cornea need to be ablated to correct any refractive abnormalities. The DOE 40 consists of a 512×512 matrix of elements with individual elements being selected from any of the elements 54–60 as shown in FIG. 2. The darker the area is in FIG. 4 the more the phase of the incident wave or ray is shifted. The lighter the area is in FIG. 4 the less the phase of the incident wave or ray is shifted. The 512×512 matrix of elements was generated by the far-field focal point of the eye 16. The DOE 40 can be constructed by using known holographic and microelectronic techniques. A continuous profile kinoform or phase only DOE can be designed for optimal efficiency and continuity in profile modulation of the incident wavefront. An example of phase optimization of a kinoform is described in an article entitled "Phase optimization of a kinoform by simulated annealing" by N. Yoshikawa and T. Yatagai, Applied Optics, Volume 33, Number 5, Feb. 10, 1994, which is incorporated herein by this reference. An example of a DOE being constructed from liquid crystals is described in an article entitled "Ferroelectric liquid-crystal spatial light modulator achieving bipolar image operation and cascadability" by S. Fukushima, T. Kurokawa, and M. Ohno, Applied Optics, Volume 31, Number 32, Nov. 10, 1992, which is incorporated herein by this reference.

Figure 5:
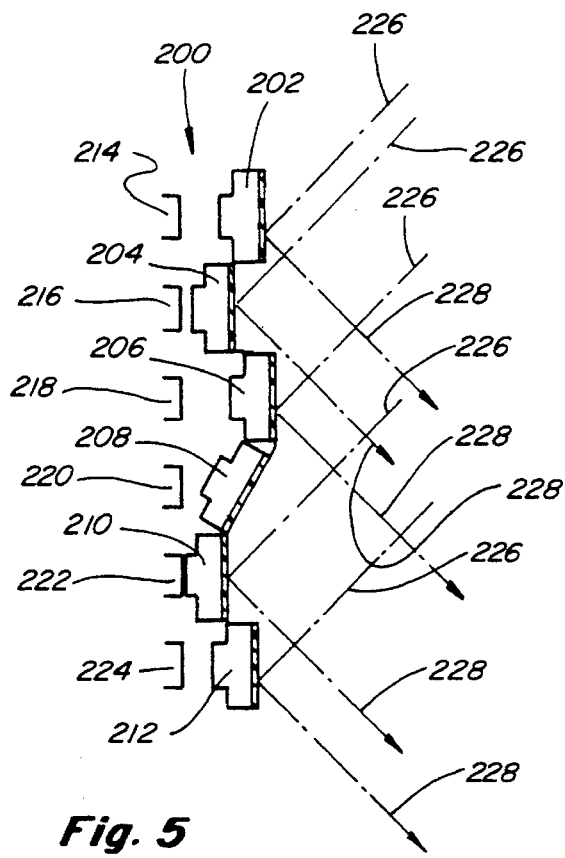
FIG. 5 is a cross-sectional view of another diffractive optical element constructed according to the present invention.

Referring now to FIG. 5, another example of a diffractive optical element (DOE) 200 is shown. DOE 200 includes of a matrix of reflective type elements 202–212 which are designed to modulate the incident flux of a beam of light in a real-time DOE system. The matrix of elements 202–212 are individually controlled by a respective coupled transducer 214–224. Each of the coupled transducers 214–224 can control the positioning of each of the elements 202–212 which provides translational freedom of each of the elements 202–212. By varying the spatial position of each of the elements 202–212 phase modulation can be imposed on the incident wavefront such as a beam of light. Additionally, by changing the angle of incidence of each of the elements 202–212 amplitude modulation can be accomplished and the amplitude of the incident wavefront can be changed. The DOE 200 is an example of a reflective type DOE. An example of how to fabricate or manufacture the DOE 200 is described in an article entitled "Mirrors on a chip" by J. Younse, IEEE Spectrum, November 1993. Additionally, an incident beam or wavefront 226 directed at the DOE 200 will be reflected by the DOE 200 as a modulated beam or wavefront 228. The modulated wavefront 228 is used to ablate a cornea.

Figure 6:
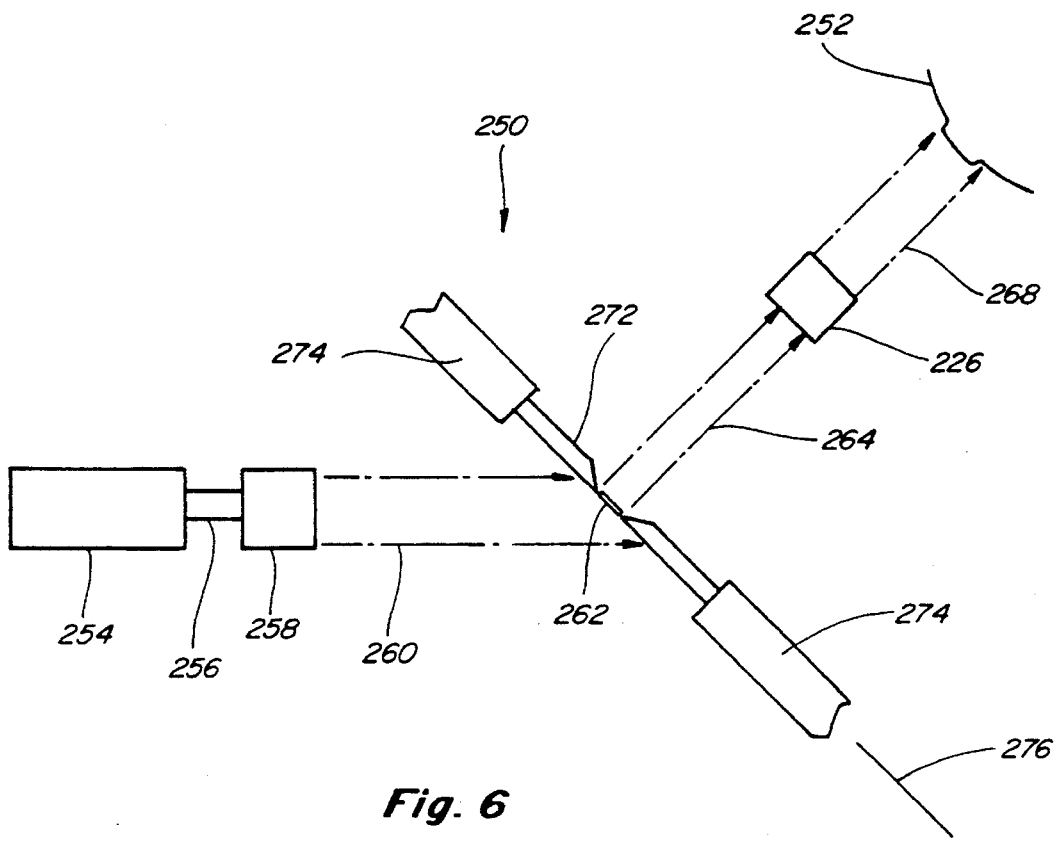
FIG. 6 is a schematic view of a transmission type system for sculpting a cornea using a diffractive optical element.

Referring now to FIG. 6, a transmission type system 250 for sculpting a cornea using a diffractive optical element is illustrated. In FIG. 6, the system 250 is used to ablate a cornea 252. A source 254, such as a laser, produces a flux distribution 256 of set intensity. The flux distribution 256 is then provided to a beam controller system 258 which produces a controllable working flux density 260. A diffractive optical element (DOE) 262 having a suitable predefined or precharacterized distribution is placed in the path of the controllable working flux density 260. The manner in which the DOE 262 is constructed is similar to the DOE 40 which was discussed with reference to FIG. 2. The DOE 262 provides a modulated flux distribution 264 to a beam controller system or a focusing system 266. The focusing system 266 is used to control the focal point of the DOE 262 in the near-field or in the far-field. The focusing system 266 produces an incident beam or wavefront 268 which is directed at the cornea 252. The modulated flux distribution 264 is focused on to the cornea 252 through the beam controller system 266 and the incident beam 268 is used to ablate the cornea 252.

A pair of supporting members 270 and 272 is used to hold the DOE 262 in place. The supporting members 270 and 272 are composed of a material which does not allow retransmission of the controllable working flux density 260. The supporting members 270 and 272 are connected to a vibrating platform 274 which provides for translation, positioning, or movement of the DOE 262 in the vertical, horizontal, or azimuthal direction about an axis 276. Movement of the DOE 262 by the vibrating platform 274 allows for greater control over the incident beam 268 and improves the power distribution at the cornea 252.

The cornea 252 is initially viewed by a topography instrument, such as the topography instrument 12 which was discussed in conjunction with FIG. 1. Once the topography of the cornea 252 has been determined this information is provided to a computer system, such as the computer system 18 which was disclosed with reference to FIG. 1. The computer system is programmed to analyze the information to determine which areas of the cornea 252 need to be ablated. Once these areas to be ablated have been determined from information provided by the computer system the DOE 262 is constructed to correspond to the profile of the cornea 262 to be ablated to correct any abnormal refractive errors.

Figure 7:
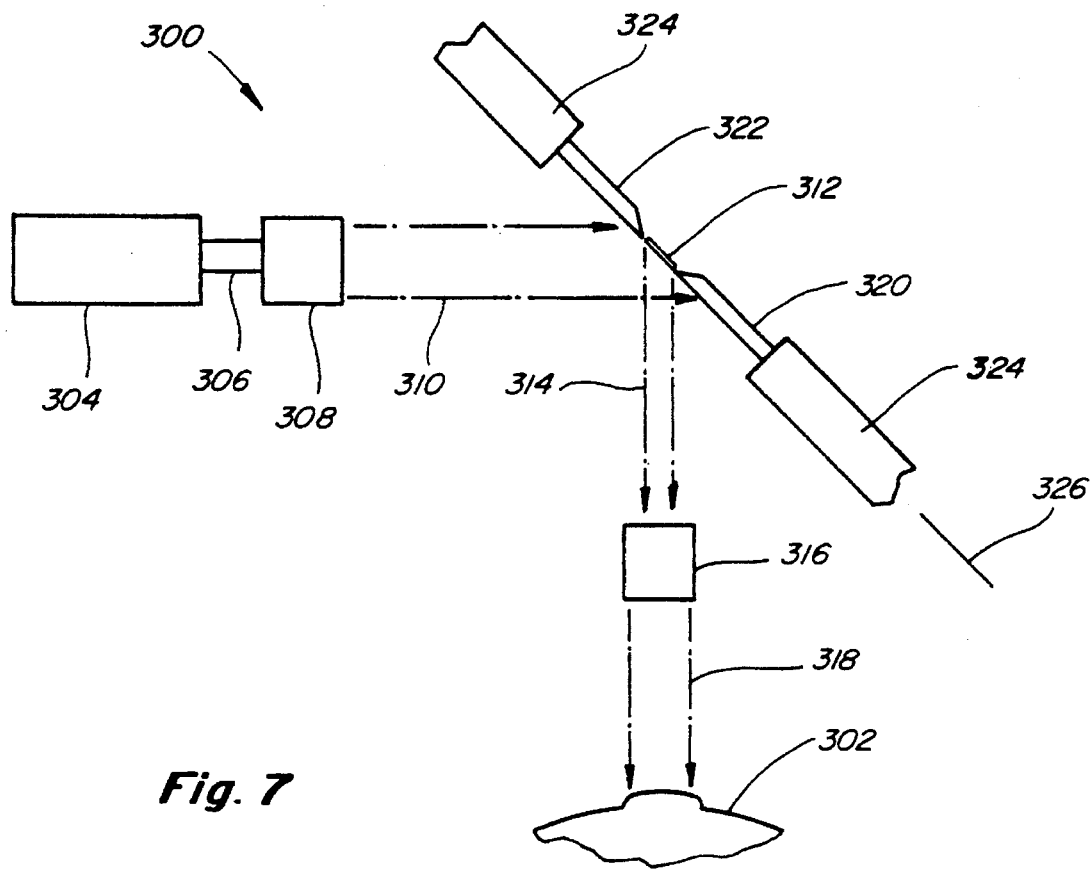
FIG. 7 is a schematic view of a reflective type system for sculpting a cornea using a diffractive optical element.

Referring now to FIG. 7, a reflective type system 300 for sculpting a cornea using a diffractive optical element is illustrated. In FIG. 7, the system 300 is used to ablate a cornea 302. A source 304, such as a laser, produces a flux distribution 306 of set intensity. The flux distribution 306 is then provided to a beam controller system 308 which produces a controllable working flux density 310. A diffractive optical element (DOE) 312 having a suitable predefined or precharacterized distribution is placed in the path of the controllable working flux density 310. The manner in which the DOE 312 is constructed is similar to the DOE 200 which was discussed with reference to FIG. 5. The DOE 312 reflects the controllable working flux density 310 and provides a modulated flux distribution 314 to a beam controller system or a focusing system 316. The focusing system 316 is used to control the focal point of the DOE 312 in the near-field or in the far-field. The focusing system 316 produces an incident beam or wavefront 318 which is directed at the cornea 302. The modulated flux distribution 314 is focused on to the cornea 302 through the beam controller system 316 and the incident beam 318 is used to ablate the cornea. 302.

A pair of supporting members 320 and 322 is used to hold the DOE 312 in place. The supporting members 320 and 322 are composed of a material which does not allow reflection of the controllable working flux density 310. The supporting members 320 and 322 are connected to a vibrating platform 324 which provides for translation, positioning, or movement of the DOE 312 in the vertical, horizontal, or azimuthal direction about an axis 326. Movement of the DOE 312 by the vibrating platform 324 allows for greater control over the incident beam 318 and improves the power distribution at the cornea 302.

The cornea 302 is initially viewed by a topography instrument, such as the topography instrument 12 which was discussed in conjunction with FIG. 1. Once the topography of the cornea 302 has been determined this information is provided to a computer system, such as the computer system 18 which was disclosed with reference to FIG. 1. The computer system is programmed to analyze the information to determine which areas of the cornea 302 need to be ablated. Once these areas to be ablated have been determined from information provided by the computer system the DOE 312 is constructed to correspond to the profile of the cornea 302 to be ablated to correct any abnormal refractive errors.

Figure 8:
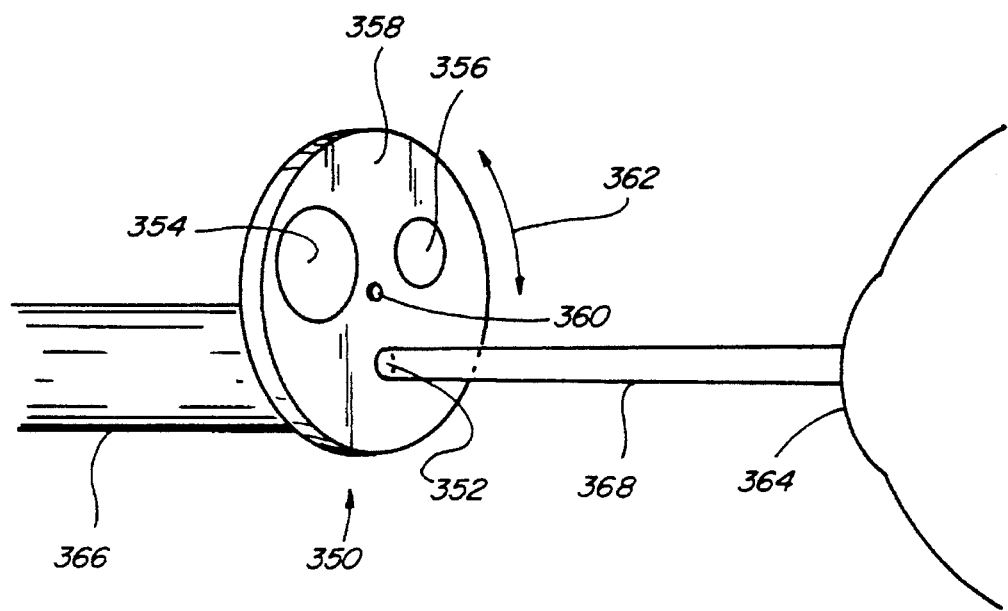
FIG. 8 is a schematic view of a preferred embodiment of a diffractive optical element system which may be used with the apparatus shown in FIG. 1.

FIG. 8 depicts a schematic view of another preferred embodiment of a diffractive optical element (DOE) system 350 which may be used in the apparatus 10 of the present invention. The DOE system 350 consists of three separate diffractive optical elements 352, 354, and 356 incorporated within a disk 358. The disk 358 is mounted on a centrally located spindle 360. The DOEs 352, 354, and 356 may be spaced circumferentially about the disk 358. The disk 358 can be rotated by the spindle 360 in either the clockwise or counterclockwise directions as indicated by the curved double headed arrow 362. In this manner an incident beam 366 may be modulated by any one of the DOEs 352, 354, and 356 by rotation of the disk 358. Once the incident beam 368 is modulated by for example DOE 352 a modulated beam 368 exits from the DOE 352 and is directed at the cornea 364 to irradiate the cornea 364. A focusing system (not shown) similar to focusing system 26 may be employed to focus the modulated beam 368. By using the disk 358 having separate DOEs a different intensity of laser radiation strikes the cornea 364 to ablate the cornea 364 in steps or stages. This cumulative effect may be desired wherein it is advantageous to remove layers of the cornea 364 in steps instead of all at once. The DOE system 350 is an example of a serial transmission type system having multiple DOEs. It is to be understood that it is also possible and contemplated to have a serial reflective type system having a disk incorporating multiple DOEs.

Figure 9:
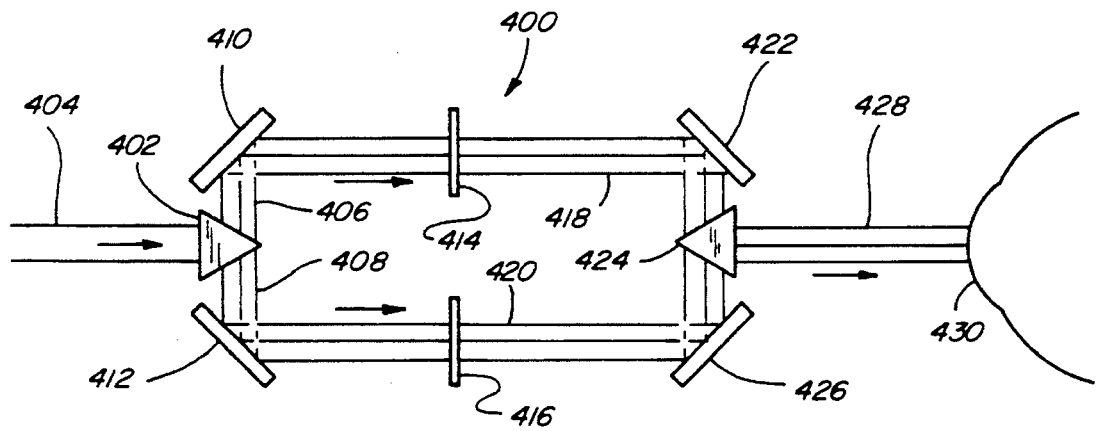
FIG. 9 is a schematic view of a second preferred embodiment of a diffractive optical element system which may be used with the apparatus shown in FIG. 1.

Referring now to FIG. 9, a schematic view of another preferred embodiment of a diffractive optical element (DOE) system 400 is shown which may be used in the apparatus 10 of the present invention. The system 400 includes a beam splitter 402 which is used to split an incoming beam 404 into two component beams 406 and 408. The component beams 406 and 408 are then each directed at reflective members 410 and 412, respectively. The reflective members 410 and 412 reflect the component beams 406 and 408 at DOEs 414 and 416, respectively. Each of the DOEs 414 and 416 has a preselected matrix of elements which modulates each of the component beams 406 and 408. The DOEs 414 and 416 are similar in construction to the DOE 40 shown in FIG. 2. Modulated component beams 418 and 420 are transmitted from the DOEs 414 and 416, respectively. The modulated component beam 418 is directed at a reflective member 422 which reflects the modulated component beam 418 to a beam splitter 424. The modulated component beam 420 is directed at a reflective member 426 which reflects the modulated component beam 420 to the beam splitter 424. The beam splitter 424 combines the reflected modulated component beams 418 and 420 into a single modulated beam 428 which is transmitted to a cornea 430 which needs to be ablated. The single modulated beam 428 is used to ablate the cornea 430. A focusing system (not shown) similar to focusing system 26 may be employed to focus the single modulated beam 428. The system 400 is an example of a parallel type system.

Figure 10:
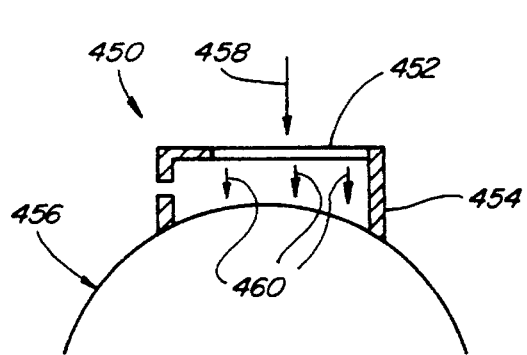
FIG. 10 is a schematic view of a third preferred embodiment of a diffractive optical element system which may be used with the apparatus shown in FIG. 1.

FIG. 10 illustrates a schematic view of another preferred embodiment of a diffractive optical element (DOE) system 450 adapted to be used with the apparatus 10 of the present invention. The DOE system 450 includes a DOE 452 which is similar to the DOE 40. The DOE 452 is incorporated within a support structure 454 which is of a size, shape, and material that allows the support structure 454 to rest above a cornea 456 to be ablated. An incident laser beam or wavefront 458 is directed at the DOE 452 to be modulated by the DOE 452. The modulated wavefront 460 is then transmitted to the cornea 456 for ablating the cornea 456.

Figure 11:
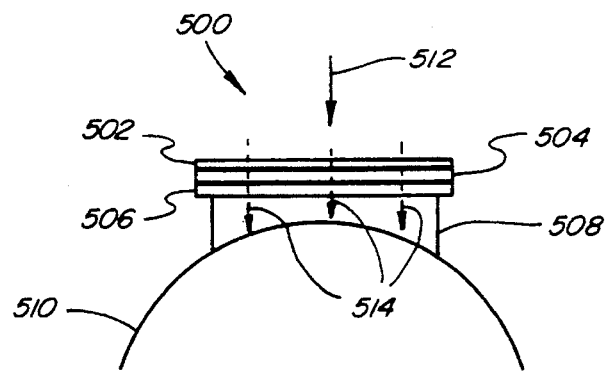
FIG. 11 is a schematic view of a fourth preferred embodiment of a diffractive optical element system which may be used with the apparatus shown in FIG. 1.

FIG. 11 illustrates a schematic view of another preferred embodiment of a diffractive optical element (DOE) system 500 adapted to be used with the apparatus 10 of the present invention. The DOE system 500 includes three DOEs 502, 504, and 506 which are stacked on top of each other. Each of the DOEs 502, 504, and 506 are similar in construction to the DOE 40. The DOEs 502, 504, and 506 are incorporated within a support structure 508 which is of a size, shape, and material that allows the support structure 508 to rest above a cornea 510 to be ablated. An incident laser beam or wavefront 512 is directed at the DOEs 502, 504, and 506 to be modulated by the DOEs 502, 504, and 506. A modulated wavefront 514 is then transmitted to the cornea 510 for ablating the cornea 510.

From all that has been said, it will be clear that there has thus been shown and described herein a laser surgical apparatus for sculpting a cornea using a diffractive optical element which fulfills the various objects and advantages sought therefor. It will apparent to those skilled in the art, however, that many changes, modifications, variations, and other uses and applications of the subject laser surgical apparatus for sculpting a cornea using a diffractive optical element are possible and contemplated. All changes, modifications, variations, and other uses and applications which do not depart from the spirit and scope of the invention are deemed to be covered by the invention, which is limited only by the claims which follow.

What is claimed is:

1. An apparatus for profiling a cornea of an eye, the cornea having an initial profile and a desired profile with the desired profile for correcting any abnormalities of the cornea, the apparatus comprising:

means for producing and projecting a beam of radiation, the beam of radiation having a wavelength, a phase, and an amplitude; and a diffractive optical element which is representative of the desired profile of the cornea, the diffractive optical element comprising a substrate having a thickness, a reference axis, and a matrix of elements formed thereon, each of the elements having a preselected reflective index, length, width, thickness, and an angle relative to the reference axis with an element having a thickness greater than the thickness of the substrate producing an exit beam of radiation having the same amplitude and phase as the beam of radiation, an element having a thickness less than the thickness of the substrate producing an exit beam of radiation having a phase that is shifted when compared to the phase of the beam of radiation, and an element having a coating applied to the substrate producing an exit beam of radiation having a phase and amplitude that are shifted when compared to the phase and amplitude of the beam of radiation, and when the beam of radiation is projected at the diffractive optical element each of the elements within the matrix produces an exit beam which is directed at the cornea for selectively ablating the cornea for profiling the cornea to the desired profile which corrects any abnormalities of the cornea.

2. The apparatus of claim 1 further comprising means for determining the curvature of the cornea and for determining whether any areas of the cornea need to be ablated to correct for any abnormalities of the cornea and wherein the determining means comprises a topography instrument which is adapted to determine the curvature of the cornea.

3. The apparatus of claim 2 wherein the determining means further comprises a computer for receiving information from the topography instrument, the information being representative of the curvature of the cornea, and the computer for determining which portions of the cornea need to be ablated to correct for any abnormalities of the cornea.

4. The apparatus of claim 1 wherein the diffractive optical element further comprises an element having an angle of incidence relative to the reference axis of the substrate which produces an exit beam of radiation having a phase and amplitude that are shifted when compared to the phase and amplitude of the beam of radiation.

5. The apparatus of claim 1 wherein the element capable of producing an exit beam of radiation having the same amplitude and phase as the beam of radiation has a thickness being an integral multiple of $2\pi$ the wavelength of the beam of radiation.

6. The apparatus of claim 1 wherein the elements within the matrix of elements are transmissive.

7. An apparatus for profiling a cornea of an eye comprising:

a topography instrument for measuring the curvature of the cornea;

a computer system connected to the topography instrument for receiving information from the topography instrument which is representative of the curvature of the cornea and for determining whether any areas of the cornea need to be ablated to correct for any abnormalities of the cornea;

means for producing and projecting a beam of radiation having a phase and an amplitude; and a diffractive optical element which is representative of the profile of the cornea to be ablated, the diffractive optical element comprising a substrate having a matrix of elements formed thereon, with each one of the elements within the matrix being capable of changing the phase of the beam of radiation, changing the amplitude of the beam of radiation, and changing both the phase and amplitude of the beam of radiation, and when the beam of radiation is projected at the diffractive optical element each one of the elements produces an exit beam of radiation which is directed at the cornea for selectively ablating the cornea to correct for any abnormalities of the cornea.

8. The apparatus of claim 7 wherein the substrate of the diffractive optical element has a thickness and the element within the matrix being capable of changing the phase of the beam of radiation has a thickness different than the thickness of the substrate.

9. The apparatus of claim 7 wherein the computer system is connected to the diffractive optical element and the computer system controls each of the elements to select whether each of the elements will change the phase of the beam of radiation, change the amplitude of the beam of radiation or change both the phase and the amplitude of the beam of radiation.

10. A method of profiling a cornea of an eye, the cornea having a profile and a curvature, the method comprising the steps of:

measuring the curvature of the cornea;

determining whether any areas of the cornea need to be ablated to correct for any abnormalities of the cornea;

producing and projecting a beam of radiation at the diffractive optical element: and modulating the beam of radiation by placing inbetween the beam of radiation and the cornea a diffractive optical element which is representative of the profile of the cornea to be ablated, the diffractive optical element comprising a substrate having a matrix of elements formed thereon capable of changing the phase of the beam of radiation, at least another one of the elements within the matrix being capable of changing the amplitude of the beam of radiation, and at least another one of the elements within the matrix being capable of changing both the phase and amplitude of the beam of radiation.

11. The method of claim 10 wherein the measuring step comprises the step of using a topography instrument to measure the curvature of the cornea.

12. The method of claim 10 wherein the determining step comprises the step of using a computer system to determine which areas of the cornea need to be ablated based upon the measurement of the curvature of the cornea.

* * * * *

UNITED STATES PATENT AND TRADEMARK OFFICE
CERTIFICATE OF CORRECTION

PATENT NO. : 5,571,107
DATED : November 5, 1996
INVENTOR(S) : Shaibani et al

It is certified that error appears in the above-indentified patent and that said Letters Patent is hereby corrected as shown below:

Column 7, line 58, after "cornea" delete --.--.

Signed and Sealed this

Eighteenth Day of March, 1997

Attest:

BRUCE LEHMAN

Attesting Officer     Commissioner of Patents and Trademarks